United States Patent [19]
Brown

[11] Patent Number: 5,154,283
[45] Date of Patent: Oct. 13, 1992

[54] MOLDED SUTURE RETAINER

[75] Inventor: David L. Brown, Wallingford, Conn.

[73] Assignee: United States Surgical Corporation, Norwalk, Conn.

[21] Appl. No.: 566,263

[22] Filed: Aug. 13, 1990

[51] Int. Cl.⁵ .............................................. A61B 17/06
[52] U.S. Cl. .................... 206/63.3; 206/461; 206/471; 206/524.8
[58] Field of Search ............... 206/49, 63.3, 277, 339, 206/380, 382, 388, 461, 467, 471, 524.8

[56] References Cited

U.S. PATENT DOCUMENTS

| | | | |
|---|---|---|---|
| 3,026,656 | 3/1962 | Rumsey, Jr. | 206/524.8 |
| 3,338,401 | 8/1967 | Regan, Jr. | |
| 3,444,994 | 5/1969 | Kaepernik et al. | |
| 3,490,192 | 1/1970 | Regan, Jr. | |
| 3,759,376 | 9/1973 | Lisowski | |
| 3,815,315 | 6/1974 | Glick | |
| 3,939,969 | 2/1976 | Miller et al. | |
| 3,972,418 | 8/1976 | Schuler et al. | 206/63.3 |
| 4,014,433 | 3/1977 | Cerwin | |
| 4,063,638 | 12/1977 | Marwood | |
| 4,249,656 | 2/1981 | Cerwin et al. | |
| 4,253,563 | 3/1981 | Komarnycky | |
| 4,424,898 | 1/1984 | Thyen et al. | |
| 4,603,538 | 8/1986 | Shave | |
| 4,961,498 | 10/1990 | Kalinski et al. | 206/63.3 |
| 4,967,902 | 11/1990 | Sobel et al. | 206/63.3 |

*Primary Examiner*—David T. Fidei
*Attorney, Agent, or Firm*—Thomas R. Bremer; Peter G. Dilworth; Rocco S. Barrese

[57] ABSTRACT

A molded suture retainer is provided for retaining and storing long suture lengths. Both absorbable and nonabsorbable sutures fabricated from natural or synthetic materials can be advantageously retained and stored therein. The retainer is characterized by a wide spiraling oval passageway with minimal convolutions covered by a cover sheet. The length of the passageway is preferably proportional to ⅓ to ½ the overall length of the suture to be retained therein. In accordance with the method of the invention, sutures are doubled or tripled over and inserted into the retainer under vacuum. Sutures packaged in accordance with the invention exhibit fewer kinks and bends than prior packaged sutures.

20 Claims, 4 Drawing Sheets

MOLDED SUTURE RETAINER

BACKGROUND OF THE INVENTION

1. Field of the Invention

The present invention relates to packaging of sutures and, more particularly, to an improved package and method of packaging sutures to improve handling characteristics thereof.

2. Description of the Related Art

This invention relates to molded suture retainers and their use for packaging sutures, including nonabsorbable and synthetic absorbable sutures, to improve the out of package flexibility and handling characteristics of the sutures after storage. Sutures can be either monofilament or braided and are available in a wide variety of materials including cotton, silk, stainless steel, catgut, and dacron, nylon or other synthetic materials.

Synthetic absorbable sutures are typically formed using polymers and copolymers of glycolic acid (i.e., hydroxyacetic acid), the cyclic dimer of glycolic acid ("glycolide"), lactic acid, the cyclic dimer of lactic acid ("lactide") and related monomers, polydioxanone, polytrimethylene carbonate, polyalkylene glycol, polycaprolactone, their copolymers, etc.

Nonabsorbable sutures may be packaged and/or sterilized using conventional techniques without concern for degradation of the suture material through hydrolysis. Synthetic absorbable sutures, in contrast, typically are packaged in moisture impervious foil laminate envelopes wherein the suture is wound in a FIG. 8 pattern on a paper retainer. Typical retainers of this type are shown in U.S. Pat. Nos. 4,249,656, 4,253,563, and 4,063,638.

Molded suture packages having narrow convoluted passageways configured to predetermine the coil of the suture are also known. For example, U.S. Pat. Nos. 3,338,401 and 3,490,192 disclose molded suture packages wherein one or more elongated sutures are retained in a coiled narrow passageway having a plurality of convolutions therein. These passageways are proportioned to accommodate an entire length of the suture end to end without folding. These passageways are typically molded into a plastic carrier material and define a small diameter hollow plastic tube. The patents also discuss the loading of sutures into the passageways using a vacuum. Molded retainers have been used to package nonabsorbable sutures, but have not been adopted for widespread use in packaging sutures.

Typical commercially available synthetic absorbable sutures are packaged under extremely dry conditions, and are relatively stiff and inflexible upon removal from the packaging. Such sutures exhibit "memory" which causes the suture to retain or resume the customary FIG. 8 or coiled shape assumed by sutures packaged in such a configuration in a cardboard or paper retainer. This effect is undesirable since the suture must be straightened prior to use. The FIG. 8 configuration has also been found to introduce undesirable kinks and binds in the suture. It is believed that the extremely dry conditions required for packaging prior synthetic absorbable sutures, together with the suture memory effect created by such packaging and the number and radius of curvature of the convolutions required to accommodate full length sutures may combine to make it difficult or impossible to withdraw the suture from such packaging without breaking the suture. This is particularly believed to be true in the case of sutures having lengths in excess of 20 inches wherein the passageways must be extremely compressed and convoluted in order to accommodate the suture end to end.

Therefore, it would be highly desirable to provide a molded suture retainer and method of loading same which permits the suture to be stored more efficiently without the introduction of kinks and bends.

Accordingly, it is one object of the invention to provide a molded suture retainer which permits easy installation, storage and removal of sutures without kinks and bends therein.

It is a further object of the present invention to provide a molded suture retainer and method of loading same which provides more efficient loading, storage and removal of long length sutures.

These and other highly desirable and unusual results are accomplished by the present invention in a molded suture retainer and method of loading same which permits the loading and storage of long length sutures and easy removal without kinks and bends.

Objects and advantages of the invention are set forth in part herein and in part will be obvious herefrom, or may be learned by practice with the invention, which is realized and attained by means of the instrumentalities and combinations pointed out in the appended claims.

The invention consists of the novel parts, constructions, arrangements, combinations, steps and improvements herein shown and described.

SUMMARY OF THE INVENTION

According to the present invention, a molded suture retainer is provided for retaining and storing sutures constructed of natural or synthetic materials including both absorbable and nonabsorbable sutures. The retainer comprises a molded member defining a wide passageway open at the top and sufficient for holding a plurality of strands of sutures therein. The passageway is formed in an oval racetrack configuration spiraling toward the interior of the retainer with a minimum number of convolutions. The length of the passageway is preferably proportional to $\frac{1}{3}$ to $\frac{1}{2}$ the overall length of the suture to be retained therein. Other proportions are also contemplated.

One end of the passageway serves as a suture receiving section to facilitate loading of the sutures. A vacuum receiving section is placed at the opposite end of the passageway to allow a vacuum to be drawn through the passageway to help position the sutures therein.

The present invention contemplates the loading and storage of both armed sutures, i.e. sutures having needles attached thereto, and unarmed sutures without needles attached.

In one embodiment of this invention, the suture is advantageously folded prior to positioning within the passageway. For double armed or long length sutures, the suture preferably is folded either in half or in thirds. Where exceptionally long sutures are contemplated, folding can be in fourths or fifths or close approximations thereof.

A cover sheet is used to overlie the open top of the retainer. The cover sheet has a vacuum aperture and suture entrance aperture formed therein. The vacuum aperture aligns and communicates with the vacuum receiving section of the passageway while the suture entrance aperture aligns and communicates with the suture receiving section of the passageway. Where desired, special needle holding sections or a foam needle part can be added to the retainer for convenient needle positioning. The cover sheet may also include a fold over section to cover the needle when packaged, but which is moved to an open position upon opening the outer pouch in order to reveal the needle.

For an armed suture, loading is accomplished by folding the suture and feeding the end opposite the needle into the suture entrance aperture. A vacuum is drawn on the passageway adjacent the vacuum aperture and serves to draw the folded suture into the passageway.

BRIEF DESCRIPTION OF THE DRAWINGS

The accompanying drawings, referred to herein and constituting a part hereof, illustrate the preferred embodiments of the product and method of the present invention, and together with the description serve to explain the principles of the invention, in which.

DETAILED DESCRIPTION OF THE PREFERRED EMBODIMENTS

Figure 1:
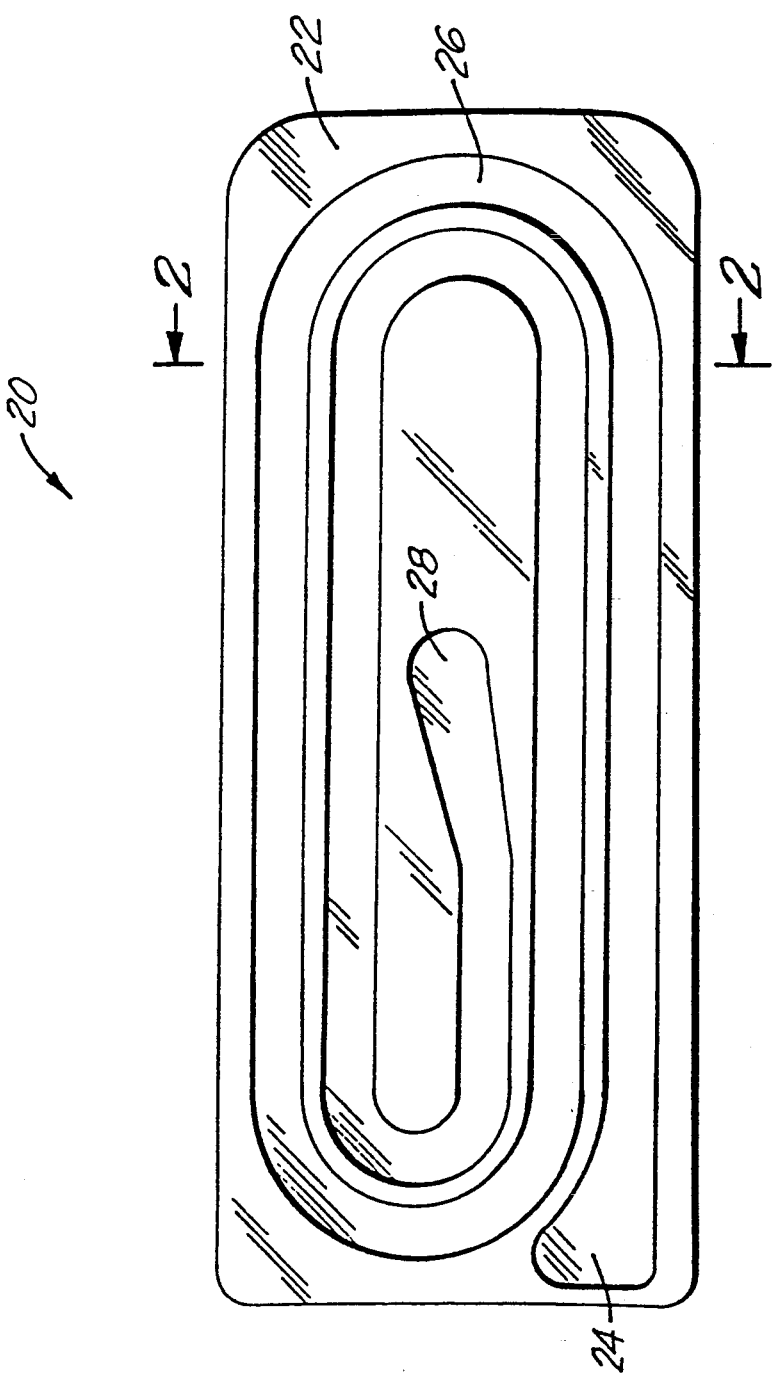
FIG. 1 is a plan view of a preferred embodiment of a molded suture retainer in accordance with the present invention.

Referring now to FIG. 1, there is shown a plan view of a molded suture retainer 20 in accordance with the invention. The molded suture retainer illustrated in FIG. 1 finds particular application for holding double or triple folded sutures of up to or more than 36 inches in length. Preferably, the molded suture retainer is made from a moldable transparent plastic material such as, for example, polyethylene terapthalate (PETG), Eastman Kodak 6763.

As shown, retainer 20 has a base 22 and an enlarged suture receiving section 24 leading to a relatively wide passageway 26 having minimal convolutions. The passageway 26 follows an oval pattern spiraling toward the proximate center through four turns and terminates at a central vacuum receiving section 28.

Figure 2:
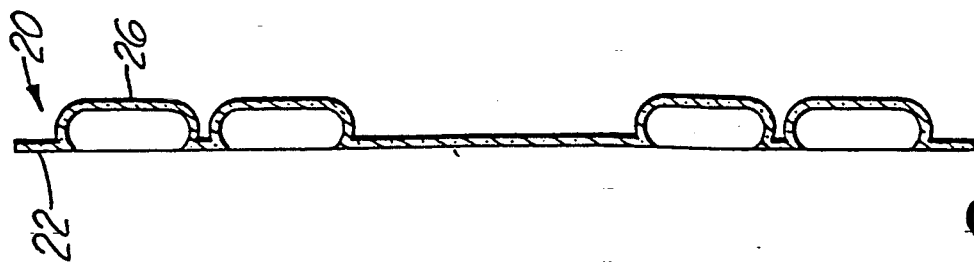
FIG. 2 is a cross-sectional view of the retainer of FIG. 1 taken along lines 2—2.

FIG. 2 is a cross-sectional view of the retainer shown in FIG. 1 taken along line 2—2 of FIG. 1, illustrating base 22 with molded passageway 26 extending from the base 22. Preferably, base 22 is approximately 3.350 inches (85.09 millimeters) by 1.375 inches (34.925 millimeters) in order to conform to commonly accepted overall dimensions of conventional suture packages and display boxes. The retainers are preferably about 0.010 inches (0.254 millimeters) thick. Typical sizes and diameters of sutures from the standard United States Pharmacopeia (United States Pharmacopeia Convention, Inc., elsewhere abbreviated U.S.P.) are listed below.

| U.S.P. Size | U.S.P. Diameter. Inches. Max. |
|---|---|
| 7-0 | 0.002 |
| 6-0 | 0.004 |
| 5-0 | 0.006 |
| 4-0 | 0.008 |
| 3-0 | 0.010 |
| 2-0 | 0.013 |
| 1-0 | 0.016 |
| 1 | 0.019 |
| 2 | 0.022 |
| 3 | 0.025 |

While these sizes are most common, one skilled in the art would realize that other sizes can be used with the retainer of the present invention. Passageway 26 is substantially wider than conventional molded suture retainer passageways and should be at least several times the diameter of the largest suture to be disposed therein. Preferably the passageway is at least about twice the diameter of the largest suture to be placed therein in depth and at least about four times the diameter in width. This relatively wide passageway 26 permits the easy insertion, storage and removal of folded sutures without the creation of undesirable kinks and bends in the suture. Depending on the size of the base and the number of sutures to be retained, the passageway may be made wider and, if necessary, deeper. For example, width ranges of between about 0.10 and 0.30 inches and depth ranges of between about 0.05 and 0.07 are contemplated. For most common suture sizes a passageway of about 0.060 inches (1.524 millimeters) deep and 0.200 inches (5.080 millimeters) wide is preferred (see FIG. 2).

Figure 3:
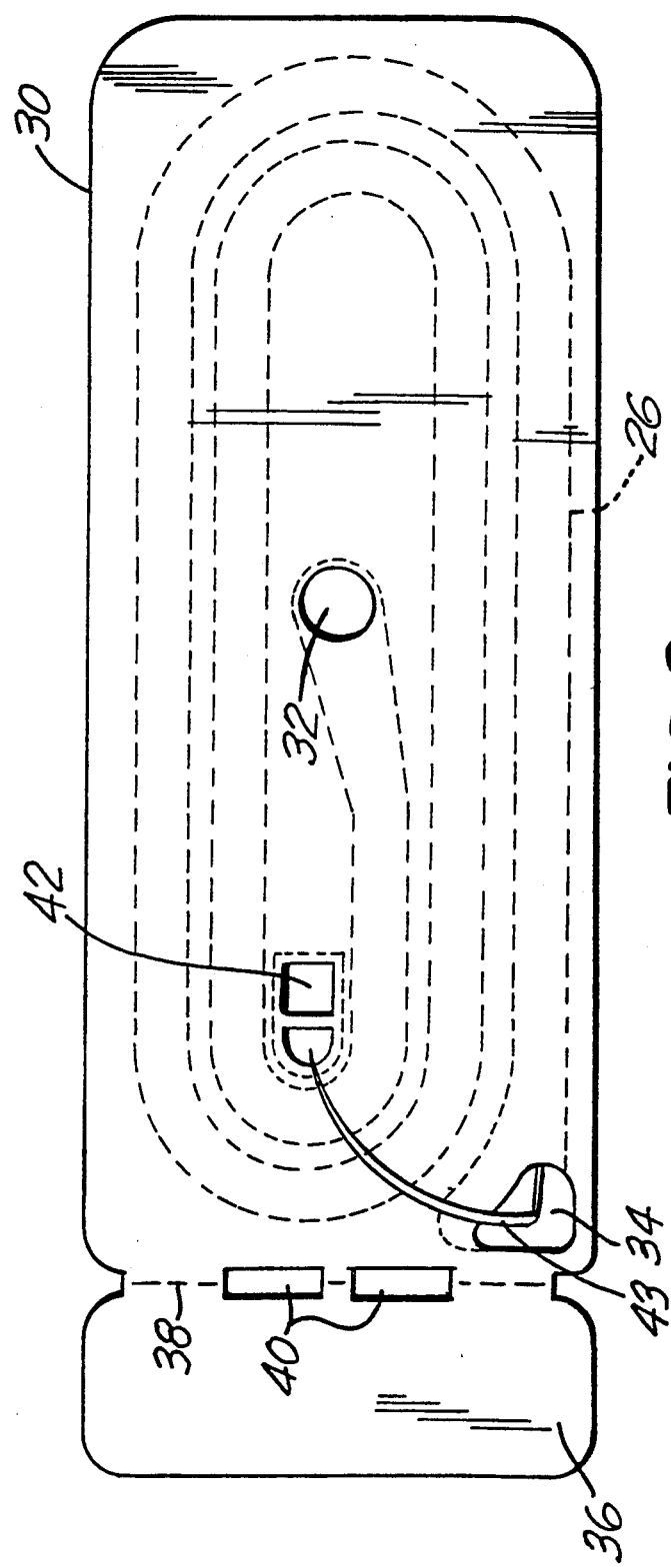
FIG. 3 is a plan view of a cover sheet for the molded suture retainer.

Referring now to FIG. 3, there is shown an appropriate cover sheet 30 for the retainer shown in FIGS. 1 and 2. Cover sheet 30 is configured and dimensioned to overlie the open top of the retainer 20. The cover sheet is provided with a vacuum aperture 32 and a suture entrance aperture 34. Cover sheet 30 is adhesively attached to the molded retainer 20 and covers the passageway 26. In a preferred embodiment the cover sheet is adhered to the retainer with a hot melt adhesive, such as Oliver 18B adhesive coating available from Oliver Products of Minneapolis, Minn.

Vacuum aperture 32 aligns and communicates with the central vacuum receiving section 28 of the molded retainer 20. Similarly, suture entrance aperture 34 aligns and communicates with the suture receiving section 24. Preferably, cover sheet 20 is constructed of a material which is pervious to ethylene oxide sterilizing gas. The preferred material is a spun bonded polyolefin, such as Tyvek 1073B available from E.I. DuPont de Nemours & Co.

As shown in FIG. 3, the preferred cover sheet 30 includes a fold-over panel 36 joined to the main section of the cover sheet at a perforated score line 38 with openings 40. Where armed sutures are to be loaded, a foam needle park 42 can be provided for holding a needle 43 in place during storage. In FIG. 3, passageway 26 is shown in phantom to illustrate the relationship of the cover sheet to the molded retainer. Retainer 20 is well suited for doubled over or doubled armed sutures and is preferred for tripled over sutures.

Figure 4:
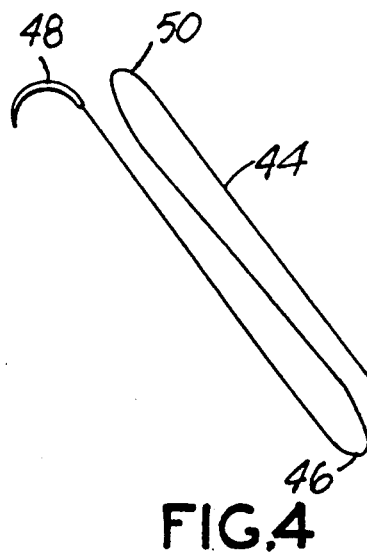
FIG. 4 is an illustration of a tripled-over suture.

Referring to FIG. 4, in order to load a tripled over suture into the retainer 20 of FIGS. 1 and 2, a suture 44, such as a suture which is thirty six or more inches in length, is looped to form a first curved or half loop section 46 distal to the needle 48 and a second curved or half loop section 50 adjacent the needle. A suture tail end 52 extends beyond the first curved section 46. Preferably, tail end 52 extends beyond first curved loop section by a distance of at least about one inch.

Figure 5:
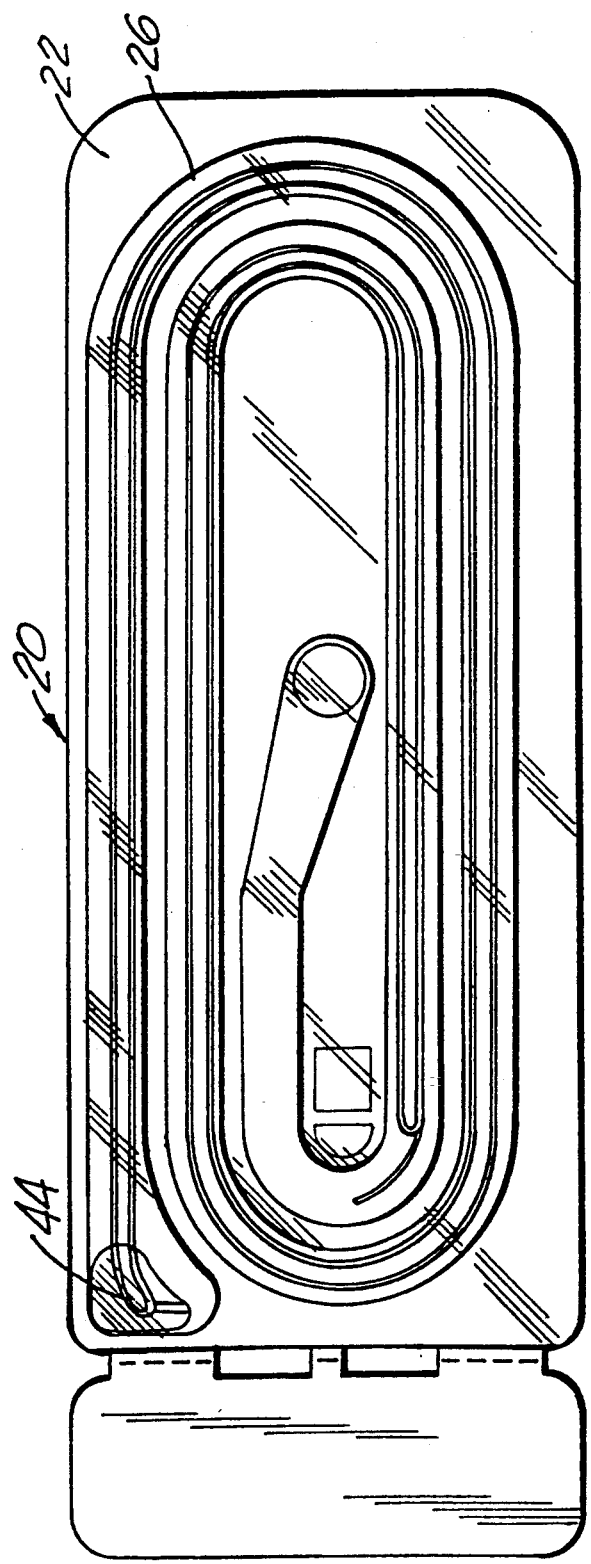
FIG. 5 is a plan view of a molded suture retainer showing a tripled over suture loaded therein.

With vacuum applied to the retainer, such as by placing a vacuum block (not shown) over vacuum aperture 32 (see FIG. 3), suture tail end 52 and then first curved section 46 are sequentially inserted through suture entrance aperture 34 into passageway 26 while holding the suture adjacent the needle 48 and the second curved section 50. The suture is drawn into the retainer 20 by vacuum until the needle 48 is disposed adjacent suture aperture 34. In this embodiment, it is important that suture tail end 52 extend beyond the first curved section 46 at all times so that a knot is not inadvertently formed in the suture during insertion or removal from the retainer. FIG. 5 shows a bottom view of an unarmed tripled over suture 44 loaded within the wide passageway 26 of the molded suture retainer 20.

Figure 6:
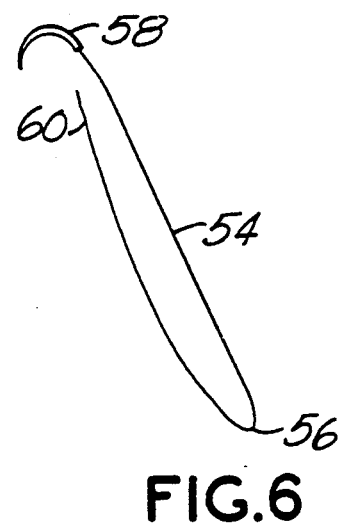
FIG. 6 is an illustration of a doubled-over suture.

For halved or doubled over sutures as shown in FIG. 6, the suture 54 is looped proximate its midpoint 56 to form two approximately equal lengths. Loading is accomplished in a manner similar to that described above with respect to the tripled over suture with the exception that no extended suture tail end need be formed. With vacuum applied, needle 58 and suture end 60 are grasped while inserting midpoint suture loop 56 through suture entrance aperture 34 into passageway 26. The suture 54 is drawn into the retainer 20 by vacuum until the needle is disposed adjacent the suture aperture 34.

Where sutures without needles are to be loaded into retainers, the above described loading procedures are equally applicable. Instead of inserting the suture until the needle is disposed adjacent the suture aperture, however, a short length of suture is maintained outside the suture aperture to facilitate easy removal. Similarly, for double armed sutures, i.e. sutures having needles on either end of the suture, the folding and loading procedure is the same as that described above for the halved suture 54 of FIG. 6, the only difference being the inclusion of a second needle at the suture end 60.

As an alternate insertion technique for double armed needles, it is contemplated that one needle could be disposed in the needle park prior to drawing the suture into the retainer under vacuum. That is, one needle would be placed in the needle park with the blunt end of the needle adjacent suture entrance aperture 34, then the suture would be drawn into the retainer under vacuum until the second needle is also adjacent the suture entrance aperture and can similarly be placed in the needle park.

Heretofore, embodiments of folded sutures have been described as being loaded singly with one suture per retainer. It is also envisaged that a plurality of these folded sutures can be loaded into and retained by a single molded suture retainer. In those cases, each of the sutures will be fed simultaneously through the suture entrance aperture 34 while a vacuum is applied to passageway 26 through vacuum aperture 32.

As stated, cover sheet 30 preferably includes a fold over panel 36. Fold over panel 36 covers the needle and suture during storage and is moved to an open position upon opening the outer package containing the suture and retainer. In the case of nonabsorbable sutures, the suture and retainer may simply be enclosed in a so-called breather pouch suitable for gas sterilization, such as a pouch consisting on one side of polyolefin (Tyvek) and a clear plastic on the other, such as polyethylene. The breather pouch is opened by peeling the two sides of the breather pouch apart and opening the fold over panel to reveal the needle or suture end, which may be grasped to remove the suture from the retainer by pulling.

Figure 7:
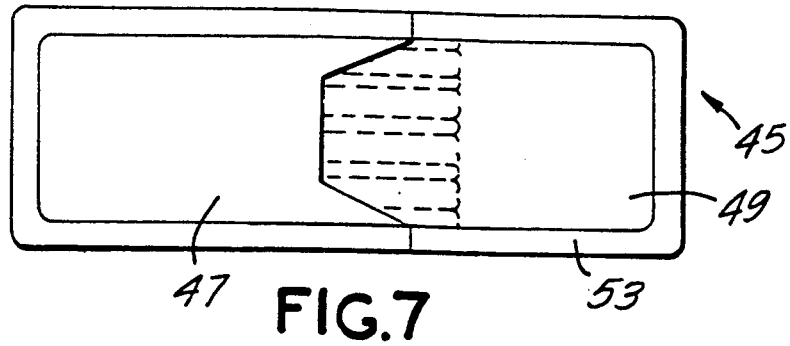
FIG. 7 is a plan view in partial cross section of a suture retainer in accordance with another embodiment of the invention.
Figure 8:
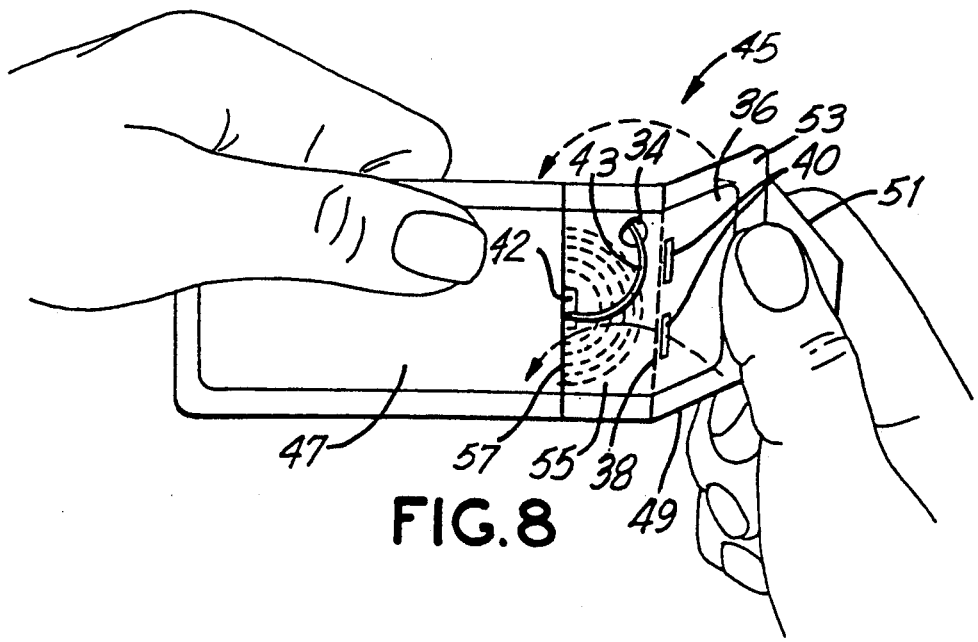
FIG. 8 is a plan view showing the opening procedure for a suture retainer in accordance with one embodiment of the invention.

In the case of synthetic absorbable sutures, the retainer would be packaged in a foil laminate envelope which would be further packaged within an outer breather pouch. The preferred inner pouch is the peelable pouch as shown in FIGS. 7 and 8. FIG. 7 is a top plan view of the preferred peelable pouch in the closed position, and FIG. 8 illustrates the pouch partially peeled open. The peelable inner pouch 45 has a top layer comprised of first and second top panels 47, 49, respectively. The first and second top panels are adhered to each other transversely, leaving a gripping tab 51. The top panels are adhered to a bottom panel 55 at a peripheral seal 53, i.e. at the transverse and longitudinal edges of the inner pouch or envelope, so as to define a pocket for receiving a suture retainer. As shown in FIG. 8, first top panel 47 does not extend the full length of bottom panel 55, but terminates at a first top panel transverse edge 57.

Upon peeling the inner pouch open, needle 43 is seen protruding from suture aperture 34 in the cover sheet and is held in position by needle park 42. The needle is plainly visible and accessible for removal of the suture from the passageway (shown in phantom) in the retainer. Preferably, fold over panel 36 is adhered to second top panel 49, so that upon opening the peelable inner pouch the needle is fully revealed and accessible. Top panels 47, 49 and bottom panel 55 may be constructed of a foil laminate material with a hot melt adhesive on the inner surface of each panel for forming peripheral seal 53 and the seal between the overlapping first and second top layer panels.

The foregoing peelable pouch is preferred, but it will be understood that other types of envelopes, such as conventional tearable foil laminate envelopes, can be used. See, for example, U.S. Pat. Nos. 3,939,969 and 4,014,433. It is contemplated that the suture could be sterilized by ethylene oxide permeating through an opening in the peelable pouch which is subsequently sealed, and that the peelable pouch itself should be sterilized and maintained sterile in an outer breather pouch in a known manner. See, for example, U.S. Pat. Nos. 3,815,315 and 4,603,538.

To the extent not already indicated, it also will be understood by those of ordinary skill in the art that any one of the various specific embodiments herein described and illustrated may be further modified to incorporate features shown in other of the specific embodiments.

The invention in its broader aspects therefore is not limited to the specific embodiments herein shown and described but departures may be made therefrom within the scope of the accompanying claims without departing from the principles of the invention and without sacrificing its chief advantages.

What is claimed is:

1. A suture retainer for packaging sutures comprising:
   a molded cover member having a spiraled passageway formed therein, said passageway defining a relatively wide channel having a width several times the diameter of a suture to be disposed therein, open at the top and having a suture receiving section formed in a proximate end thereof and a central vacuum receiving section at a distal end thereof;

a cover sheet adhered to said molded member to close said channel, said cover sheet including a vacuum aperture aligned with said central vacuum receiving section in said molded member and a suture entrance aperture aligned with said suture receiving section.

2. A suture retainer as in claim 1 further comprising a suture disposed in said passageway, said suture having at least one curved section such that portions of the suture are disposed side by side within said passageway.

3. A suture retainer as in claim 2 wherein said suture comprises a tripled over suture, said suture being folded to form a first suture curved section adjacent a distal end of said suture and a second suture curved section adjacent a proximate end of said suture, said distal end extending beyond said first suture curved section in said passageway.

4. A suture retainer as in claim 2 wherein said suture comprises a halved suture located in said passageway, said suture being folded approximately in half to form a suture curved section, said suture curved section being located in said passageway distal from said suture receiving section.

5. A suture retainer as in claim 1 wherein said relatively wide passageway is at least about twice the diameter of the largest suture to be placed therein in width and at least about four times the diameter in width.

6. A suture retainer as in claim 1 wherein said relatively wide passageway is between about 0.10 and 0.30 inches wide and between about 0.05 and 0.07 inches deep.

7. A suture retainer as in claim 1 further comprising a fold over panel attached to said cover sheet.

8. A suture retainer as in claim 1 wherein said cover sheet is constructed of a material which is pervious to ethylene oxide sterilizing gas.

9. A suture retainer as in claim 1 wherein said molded member is formed from a moldable transparent plastic material.

10. A suture retainer as in claim 1 wherein said spiraled passageway is configured in an oval pattern spiraling annularly toward the proximate center of said molded member.

11. A suture retainer as in claim 2, said suture further comprising a needle fixed to said proximate end of said suture.

12. A suture retainer as in claim 2, said suture being constructed of nonabsorbable material.

13. A suture retainer as in claim 2, said suture being constructed of absorbable material.

14. A suture retainer as in claim 5 wherein said wide passageway is approximately 0.20 inches wide and approximately 0.06 inches deep.

15. A suture retainer as in claim 1 wherein said cover sheet is constructed of a spun bonded polyolefin.

16. A suture retainer as in claim 9 wherein said molded member is constructed of polyethylene teraphthalate.

17. A suture retainer as in claim 1 further comprising a needle park disposed on and attached to said cover sheet.

18. A suture retainer as in claim 4 further comprising first and second needles fixed to opposite ends of said suture, said suture being disposed in said passageway with said curved section distal to said suture receiving section, said needles protruding from said suture receiving section to facilitate removal of said suture from the retainer.

19. A suture package for packaging sutures comprising a suture retainer having:
a molded cover member having a spiraled passageway formed therein, said passageway defining a relatively wide channel having a width several times the diameter of a suture to be disposed therein, open at the top and having a suture receiving section formed in a proximate end thereof and a central vacuum receiving section at a distal end thereof;
a cover sheet adhered to said molded member to close said channel, said cover sheet including a vacuum aperture aligned with said central vacuum receiving section in said molded member and a suture entrance aperture aligned with said suture receiving section;
a peelable pouch having first and second walls adhered to each other along their edges to define an accessible pocket therebetween for receiving said suture retainer and a closure flap hingedly adhered to a peripheral portion of said first wall and sealing access to said pocket of said peelable pouch, said closure flap terminating in a grip-facilitating tab, whereby said inner pouch is opened in a single step by opening of said closure flap, allowing access to the suture contained in said retainer.

20. A suture package as in claim 19 wherein said cover sheet includes a fold over panel, said fold over panel being adhered to said closure flap such that said fold over panel is moved away from said suture as said closure flap is opened, thereby revealing and providing access to said suture.

* * * * *